United States Patent [19]
Umeyama et al.

[11] Patent Number: 5,702,384
[45] Date of Patent: Dec. 30, 1997

[54] APPARATUS FOR GENE THERAPY

[75] Inventors: Koichi Umeyama, Kasukabe; Tadahiko Ogasawara, Tokyo; Kenji Yoshino, Tokyo; Katsushi Watanabe, Tokyo; Koji Koda, Tokyo, all of Japan

[73] Assignee: Olympus Optical Co., Ltd., Tokyo, Japan

[21] Appl. No.: 458,910

[22] Filed: Jun. 2, 1995

Related U.S. Application Data

[62] Division of Ser. No. 291,737, Aug. 17, 1994, abandoned, which is a continuation of Ser. No. 20,318, Feb. 19, 1993, abandoned.

[30] Foreign Application Priority Data

Feb. 28, 1992 [JP] Japan ..................... 4-43773
Nov. 27, 1992 [JP] Japan ..................... 4-318656

[51] Int. Cl.$^6$ ............. A61K 9/22; C12N 15/00
[52] U.S. Cl. .......... 604/892.1; 604/173; 604/306; 435/172.1; 435/240.21
[58] Field of Search ............... 604/20, 96, 101, 604/265, 892.1, 305–308, 272, 173, 21, 51, 191, 239; 623/15; 424/DIG. 13; 435/91, 172.1, 240.21, 240.23, 240.31, 172.2; 222/108, 54, 504, 399

[56] References Cited

U.S. PATENT DOCUMENTS

| | | |
|---|---|---|
| 3,348,542 | 10/1967 | Jackson. |
| 4,150,669 | 4/1979 | Latorre ..................... 604/191 X |
| 4,301,803 | 11/1981 | Handa et al.. |
| 4,471,779 | 9/1984 | Antoshkiw et al.. |
| 4,509,523 | 4/1985 | Pevsner. |
| 4,693,243 | 9/1987 | Buras. |
| 4,695,273 | 9/1987 | Brown ..................... 604/173 |
| 5,031,613 | 7/1991 | Smith et al.. |
| 5,036,006 | 7/1991 | Sanford et al. ................. 435/170.1 |

(List continued on next page.)

FOREIGN PATENT DOCUMENTS

| | | |
|---|---|---|
| 0 381 490 | 8/1990 | European Pat. Off.. |
| 31516830 A1 | 11/1986 | Germany. |
| 89 04 026 U | 7/1989 | Germany. |
| 3821544 A1 | 12/1989 | Germany. |
| 90 05 832 U | 12/1990 | Germany. |

OTHER PUBLICATIONS

Science, vol. 249, pp. 1285–1288 (1990); "Site–Specific Gene Expression in Vivo by Direct Gene Transfer Into The Arterial Wall"; by E. Nabel et al.

Article entitled "Product Miniaturization by Micromachine Technique" Chinoka Jiten, Ed. Kabushiki Kaisha Sangyo Chosakaai Jiten Shuppan Center, pp. 41–45, May 10, 1992.

Article from Nikkei Science, Jan., 1991, pp. 36–45.

Primary Examiner—Michael Powell Buiz
Assistant Examiner—A. T. Nguyen
Attorney, Agent, or Firm—Frishauf, Holtz, Goodman, Langer & Chick

[57] ABSTRACT

There is provided an apparatus for gene therapy to transfer or introduce, in vivo, a gene for treatment into a cell located at a target portion of a patient, so that the gene can be transferred with a high probability within a short period of time. The apparatus is applicable to all cell species. In addition to simple supply of a gene to the cell of the patient, the gene is forcibly transferred to the cell without depending on natural cellular physiology. For example, catheters are mounted on a probe inserted into a body cavity, and the gene is supplied from a reservoir which stores the gene to the surface of a human living cell of the target portion in the body cavity through needle cannulas attached to the distal ends of the catheters. A pulse voltage is applied to the needle cannulas to form a pore in the surface of the human living cell upon application of the pulse voltage. The gene is transferred into the human living cell through the pore.

8 Claims, 12 Drawing Sheets

U.S. PATENT DOCUMENTS

| | | |
|---|---|---|
| 5,049,132 | 9/1991 | Shaffer et al. . |
| 5,087,244 | 2/1992 | Wolinsky et al. . |
| 5,120,657 | 6/1992 | McCabe et al. ............ 435/287 |
| 5,141,131 | 8/1992 | Miller, Jr. et al. ............ 222/54 |
| 5,204,253 | 4/1993 | Sanford et al. ............ 435/172.3 |
| 5,219,746 | 6/1993 | Brinegar et al. ............ 435/172.3 |
| 5,240,855 | 8/1993 | Tomes . |
| 5,240,885 | 8/1993 | Tomes ............ 435/287 |
| 5,273,525 | 12/1993 | Hofman ............ 604/21 |
| 5,371,015 | 12/1994 | Sanford et al. ............ 435/287 |
| 5,457,041 | 10/1995 | Ginaven et al. ............ 435/172.1 |

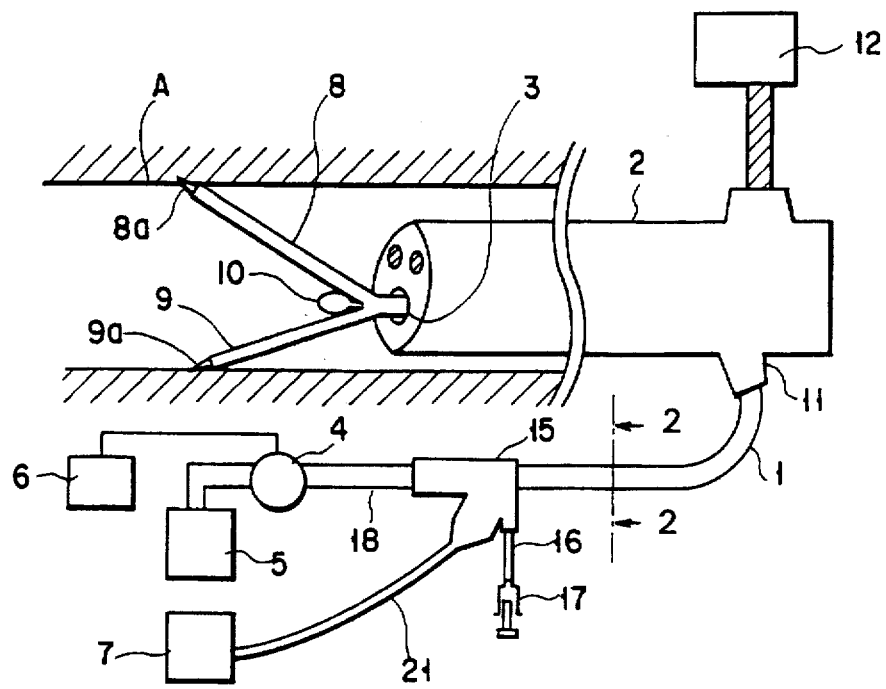
FIG. 1
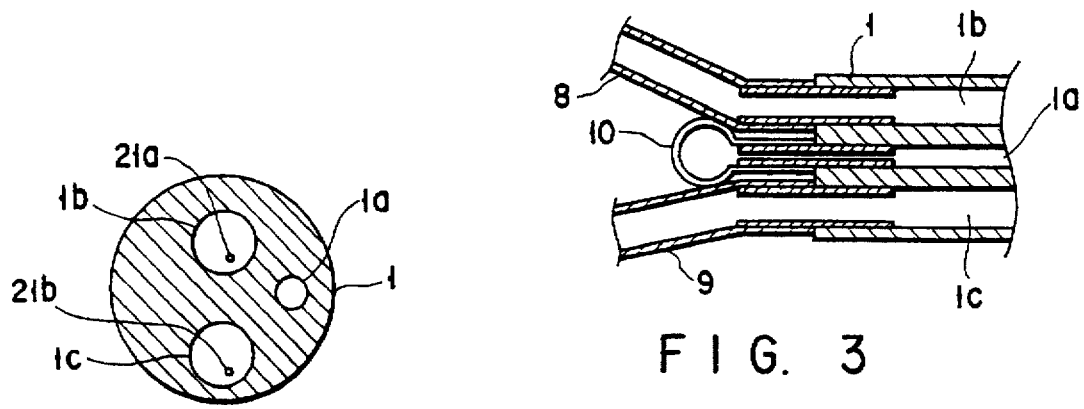
FIG. 2
FIG. 3
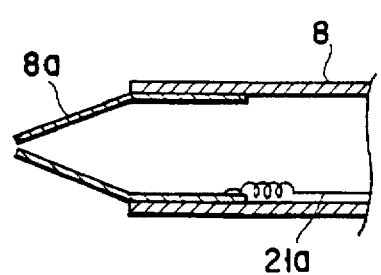
FIG. 4

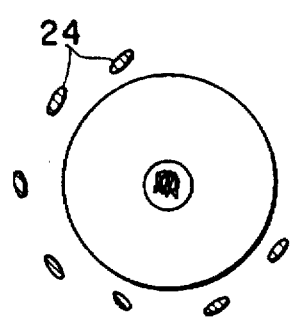
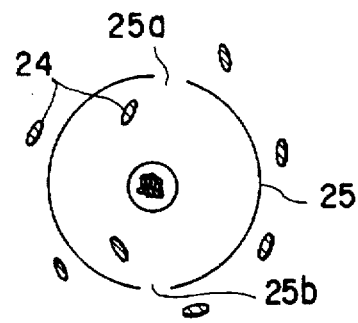
F I G. 5A  F I G. 5B
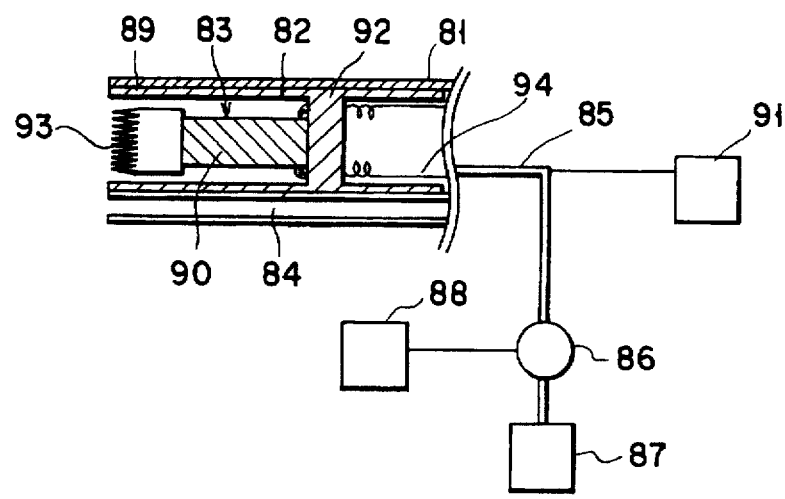
F I G. 6
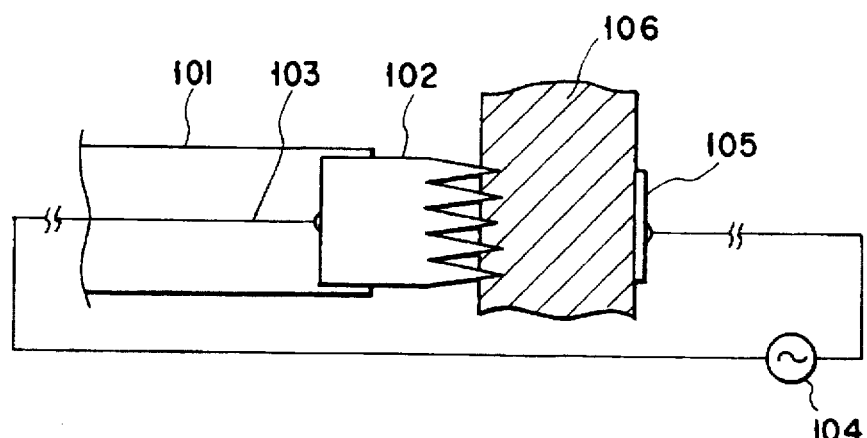
F I G. 7

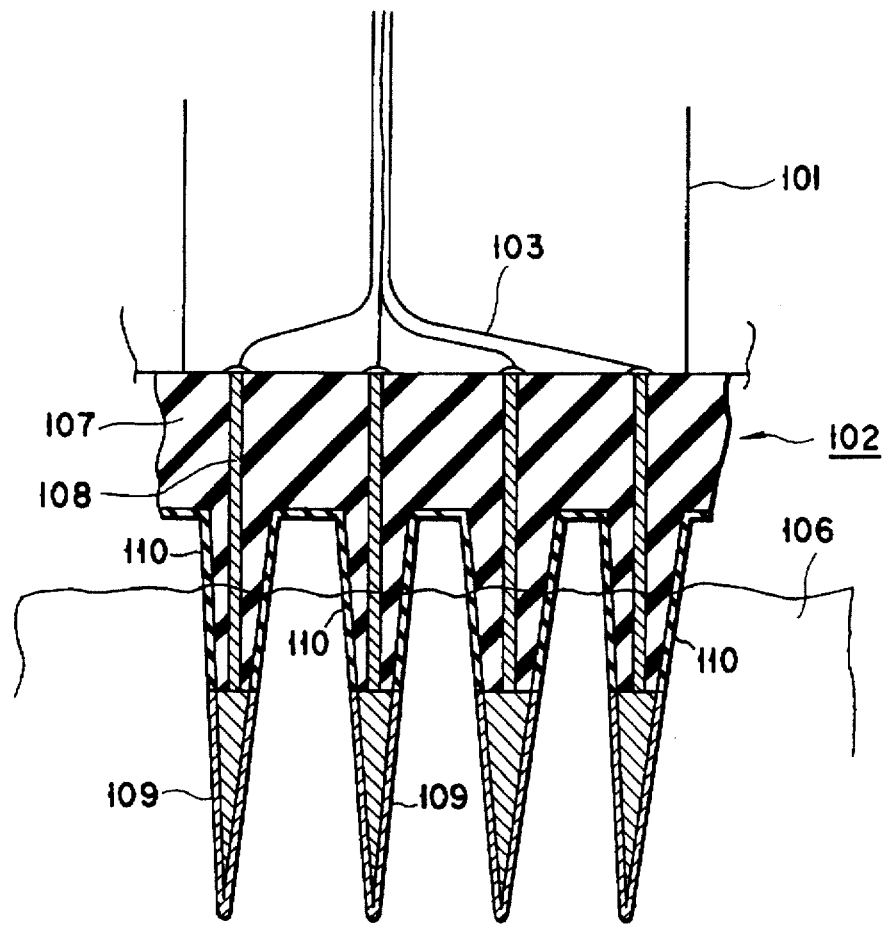
F I G. 8
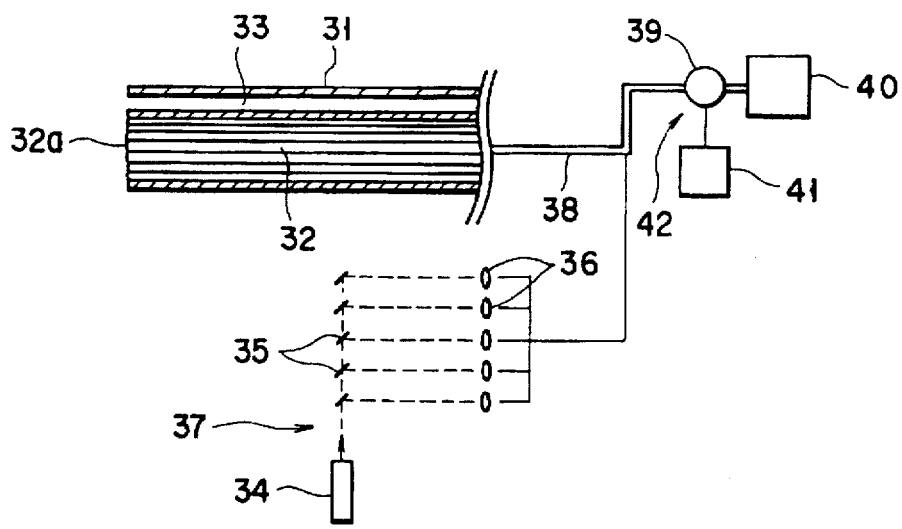
F I G. 9

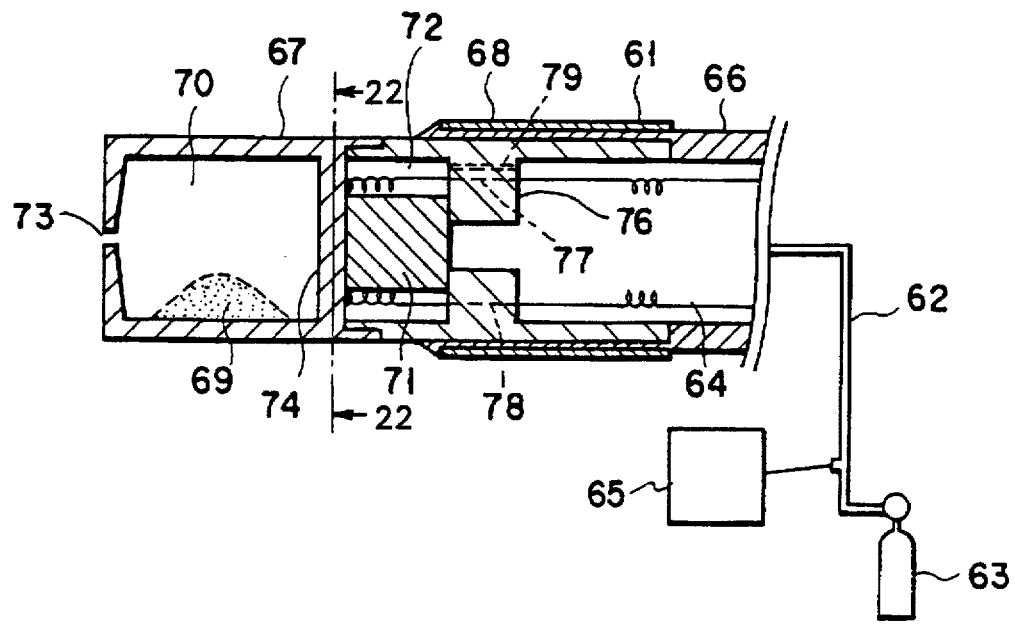
F I G. 21
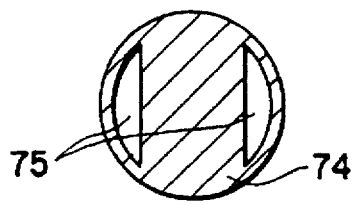
F I G. 22
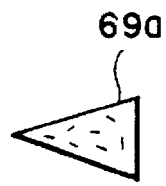 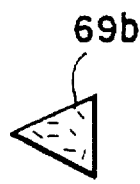
F I G. 23A    F I G. 23B

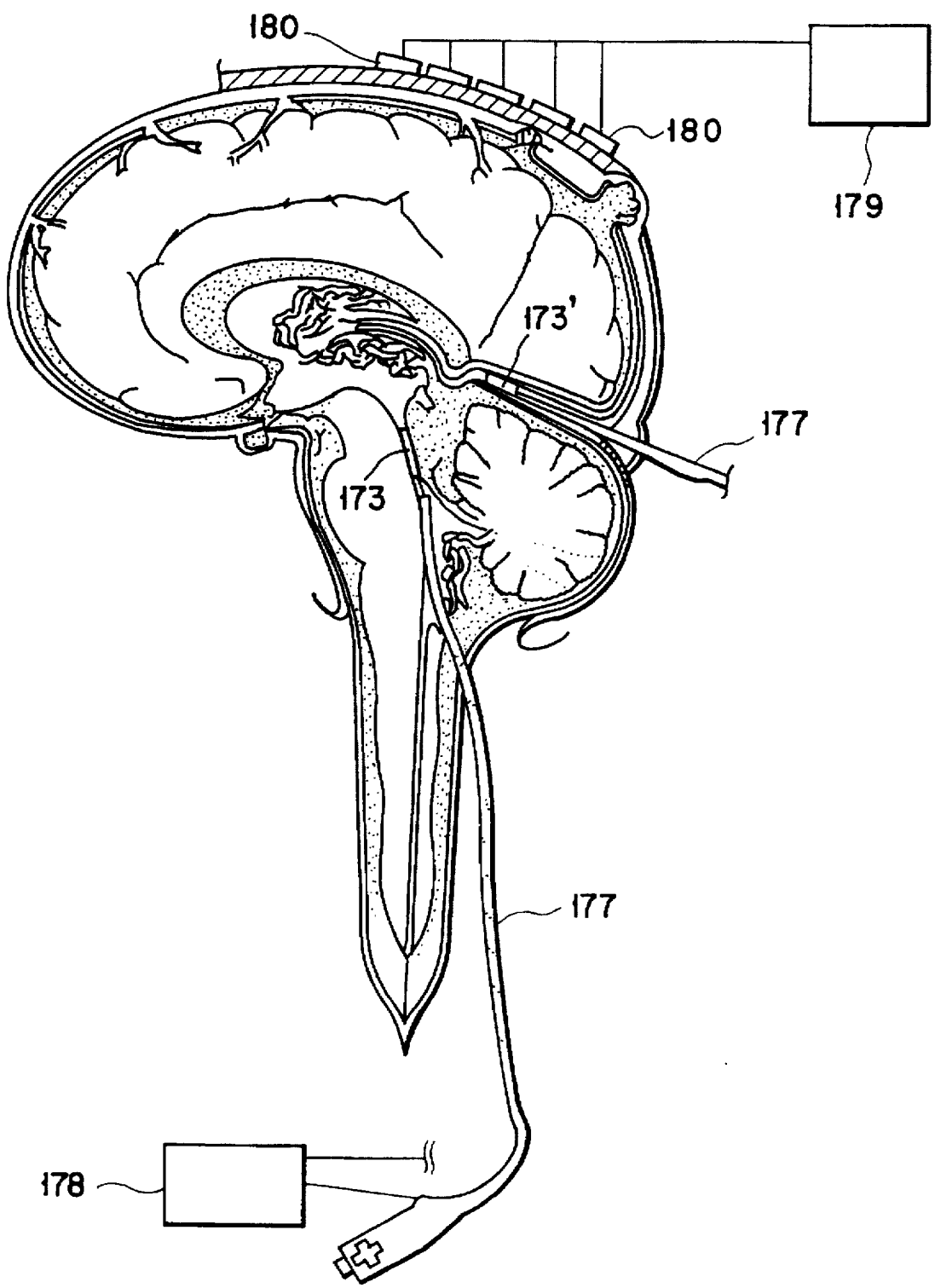
F I G. 29

APPARATUS FOR GENE THERAPY

This is a division of application Ser. No. 08/291,737 filed Aug. 17, 1994 now abandoned, which is a Continuation of application Ser. No. 08/020,318, filed Feb. 19, 1993 (abandoned).

BACKGROUND OF THE INVENTION

1. Field of the Invention

The present invention relates to an apparatus for gene therapy in which a gene or a gene-packaging particle for treatment is transferred or introduced into a human living cell in vivo through a probe inserted into a body cavity.

2. Description of the Related Art

Gene therapy is a method of treating various types of diseases by transferring or introducing a predetermined gene for treatment into a patient's cell and expressing the gene. This therapy is classified into the following two methods.

(1) One method is that of transferring a normal gene into patient's cells which are suffering from function failure due to abnormality of the gene and expressing the transferred gene, thereby repairing or restoring the impaired or lost function. This method has a possibility of drastically curing intractable diseases such as hemophilia, diabetes mellitus, hepatitis, pulmonary emphysema, arteriosclerosis, and Alzheimer's disease.

(2) The other method is that of transferring a foreign gene inherently absent in a patient into the cell and treating the disease by a special effect obtained by its expression. As an example of this gene therapy, a gene for encoding a substance effective in the treatment of a cancer (examples of which substance is cytokines capable of activating an immune system for attacking the cancer cell) is transferred into patient's cells to produce the substance upon expression of the transferred gene, thereby treating the cancer. According to this method, the therapeutic effect can be maintained for a longer period of time than a method of externally administering the same substance.

In any case of the gene therapy, it is necessary to transfer a predetermined gene for treatment (a liposome encapsulating this gene or a retrovirus integrated with this gene may be used) into a patient's cell. As a means for the gene therapy, a method of isolating human living cells, transfecting the cells with a gene for treatment, and returning the transfected cells to the human body is described in, e.g., "Nikkei Science", January, 1991.

In order to alleviate the stress and invasion of a patient in sampling cells, it is preferable to transfer a gene into a patient's cell in vivo. In gene transfection in vivo, a gene is sprayed on the surface of in vivo cells. The gene is transferred into the patient's cells in accordance with cellular physiology such as endocytosis, membrane fusion, or membrane-permeation accompanied with receptor-bonding.

As an example of in vivo gene transfection, SCIENCE, Vol. 249, P. 1285–1288 (1990) describes a method of inserting a balloon catheter into a blood vessel to stop the blood flow, spraying a gene-packaging liposome on the inner wall of the blood vessel, and leaving the sprayed gene to stand for several tens of minutes, thereby transferring the gene into the vascular endothelial cell by membrane fusion. As can be apparent from this method, in the case of in vivo gene transfection, since the transferred gene is locally expressed in the human body, an additional advantage such as reduction in side effects can be obtained.

Further, in gene therapy for a cell such as a nerve cell which cannot be extracted outside the human body in order to transfer a gene thereinto, strong demand has arisen for developments in, particularly, in vivo gene transfection.

In conventional in vivo gene transfection, a doctor only supplies a gene to the surface of the cell of a patient. Transfection of the supplied gene into the cell solely depends on the principle that the cell physiologically incorporates the gene. Therefore, the following problems are posed.

(1) Use of Endocytosis

Since the frequency of endocytosis is considerably low, it is difficult to transfer the gene into the cell.

(2) Use of Membrane Fusion

Since the membrane fusion rate is low, it takes a long period of time to transfer the gene into the cell.

(3) Use of Membrane-Permeation accompanied with Receptor-Bonding

This method cannot be used for a cell which does not have specific receptor.

SUMMARY OF THE INVENTION

The present invention has been made in consideration of the above situation, and has as its object to provide an apparatus for gene therapy which is used to transfer or introduce a gene for treatment into a cell located at a target portion of a patient in vivo and is applicable to all cell species, wherein the gene can be transferred or introduced into the cell with a high probability within a short period of time.

In order to achieve the above object of the present invention, not only supplying a gene for treatment to the cell of a patient, but also arranging a physicochemical or non-biological auxiliary means to positively promote introduction of the gene into the cell (i.e., the gene transfection of the cell).

More specifically, according to the first aspect of the present invention, there is provided an apparatus for gene therapy, comprising a probe to be inserted into a body cavity, gene supply means for supplying a gene to a surface of a human living cell located at a target portion in the body cavity, and gene transfection means, arranged at a distal end of the probe, for forming a pore in the surface of the human living cell to transfer the gene into the human living cell through the pore. The gene transfection means may be application of a pulse voltage, mechanical perforation, or radiation with a laser beam.

According to the first aspect of the present invention, using the gene transfection means arranged at the distal end of the probe, the pore is formed in the surface of the human living cell to be subjected to gene transfection. As a result, the gene having been supplied to the surface of the human living cell is transferred into the cell through the pore without depending on the cellular physiology such as endocytosis.

According to the second aspect of the present invention, there is provided an apparatus for gene therapy, comprising a probe to be inserted into a body cavity, a storage chamber, formed at a distal end of the probe and having an opening, for storing gene bullets consisting of a plurality of small pieces immobilized with a gene or containing the gene, and gene bullet shooting means for shooting the gene bullet from the opening to a surface of a human living cell located at a target portion in a body cavity upon an external operation. The gene bullet shooting means may be a means for shooting the gene bullet upon supply of a compressed gas to the gene storage chamber. The gene bullet shooting means may be a means for shooting the gene bullet in accordance with an air gun system in which the gene bullet is loaded in the opening and the pressure in the gene storage chamber is increased by a piston.

According to the second aspect of the present invention, the gene bullet stored in the storage chamber located at the distal end of the probe is shot toward the target cell by the shooting means. The shot gene bullet is transferred into the cell through the cell membrane of the target cell.

The above object can also be achieved by effectively utilizing gene incorporation due to cellular physiology. For this purpose, when a morbid portion is located deep inside the tissue, it is effective to cause the gene to permeate deep inside the tissue. In addition, the endocytosis activity can be improved by stimulating the corresponding cell.

From the above point of view, according to the third aspect of the present invention, there is provided an apparatus for gene therapy, comprising a probe to be inserted into a body cavity, a gene storage chamber arranged at a distal end of the probe, and an electrophoretic electrode for causing a gene stored in the gene storage chamber to permeate into a deep portion of a tissue by electrophoresis.

According to the third aspect of the present invention, since not only the gene is administered to the inner surface of the body cavity, but also it permeates by electrophoresis into the morbid portion located deep inside the tissue. Therefore, the gene is incorporated in the morbid cell, thereby obtaining a more desirable treatment effect.

In addition, according to the fourth aspect of the present invention, there is provided an apparatus for gene therapy, comprising means for administering a gene to a morbid tissue, and means for mechanically or physically stimulating the morbid tissue to improve an endocytosis activity of a morbid cell. The means for mechanically or physically stimulating the morbid tissue may be application of an ultrasonic wave, a radio wave, a microwave, or a magnetic field.

According to the fourth aspect of the present invention, since the endocytosis activity of the cell of the morbid tissue can be improved, the incorporation efficiency of the gene can be improved.

The gene used in the gene therapy using the apparatus according to the present invention is a gene for treatment as described previously. Examples of this gene for treatment include a gene-packaging particle such as a gene-packaging liposome and a gene-packaging retrovirus in addition to the gene itself. It is possible to use know bectors, an example of which has been described in EP 0381490A2.

The apparatus for gene therapy according to the present invention can be used in a combination with an imaging means such as an endoscope, and this combination is useful.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 1 is a view showing the overall arrangement of an apparatus for gene therapy according to the first embodiment of the present invention;

FIG. 2 is a cross-sectional view of the apparatus along the line 2—2 of FIG. 1;

FIG. 3 is a longitudinal sectional view showing part of a catheter of the embodiment shown in FIG. 1;

FIG. 4 is a longitudinal sectional view showing the distal end portion of the catheter of the embodiment shown in FIG. 1;

FIGS. 5(a) and 5(b) are views for explaining the operation of the embodiment shown in FIG. 1;

FIG. 6 is a view showing the overall arrangement of an apparatus for gene therapy according to the second embodiment of the present invention;

FIG. 7 is a view showing the overall arrangement of an apparatus for gene therapy according to the third embodiment of the present invention;

FIG. 8 is a view showing the overall arrangement of an apparatus for gene therapy according to the fourth embodiment of the present invention;

FIG. 9 is a view showing the overall arrangement of an apparatus for gene therapy according to the fifth embodiment of the present invention;

FIG. 21 is a view showing an apparatus for gene therapy according to the eleventh embodiment of the present invention;

FIG. 22 is a cross-sectional view of the apparatus along the line 22—22 of FIG. 21;

FIGS. 23(A) and 23(B) are views showing examples of gene bullets used in the apparatus for gene therapy shown in FIG. 21;

FIG. 29 is a view for explaining an application of the apparatus for gene therapy shown in FIG. 28.

DETAILED DESCRIPTION OF THE PREFERRED EMBODIMENTS

Figure 10:
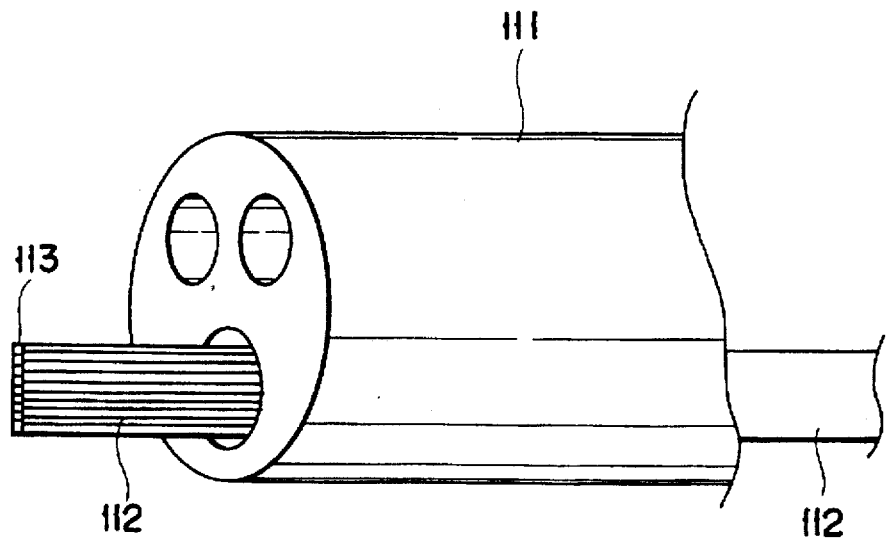
FIG. 10 is a view showing the overall arrangement of an apparatus for gene therapy according to the sixth embodiment of the present invention.

Preferred embodiments of the present invention will be described with reference to the accompanying drawings.

FIGS. 1 to 5(b) show an apparatus for gene therapy according to the first embodiment of the present invention, which is a pore forming type using electric means. FIG. 1 shows the overall arrangement of this apparatus. Referring to FIG. 1, reference numeral 1 denotes a probe. The probe 1 is inserted in an instrument channel 3 of an endoscope to be inserted into a body cavity. In this embodiment, the endoscope is an angio-endoscope 2 to be inserted into a blood vessel A. The probe 1 has an outer diameter and length sufficient to be inserted in the instrument channel 3 of the angio-endoscope 2. A quantitative discharge pump 4, a reservoir 5, a setting unit 6, and a high-voltage pulse source 7 are arranged at the proximal end of the probe 1.

As shown in FIGS. 3 and 4, the distal end portion of the probe 1 is branched into two portions to constitute two catheters 8 and 9. Tapered conical needle cannulas 8a and 9a are mounted on the distal ends of the catheters 8 and 9, respectively. An inflatable balloon 10 is clamped between the catheters 8 and 9 near the branching portion of these catheters 8 and 9.

The interior of the probe 1 has a 3-lumen structure, as shown in FIG. 2. A lumen 1a as one of the three lumens is connected so as to be capable of supplying air to the balloon 10. Remaining lumens 1b and 1c are connected so as to be capable of supplying a fluid to the catheters 8 and 9.

The probe 1 has a branching portion 15 near the point where the probe 1 is externally drawn out from a channel opening 11 of the instrument channel 3 in the angio-endoscope 2. The probe 1 branches into three tubes from this branching portion 15. The first tube extending from the branching portion 15 is an air supply tube 16. One end of the air supply tube 16 is connected to the lumen 1a of the three lumens, which is connected to the balloon 10. The other end of the air supply tube 16 is connected to a syringe 17.

The second tube extending from the branching portion 15 is a liquid supply tube 18. One end of the liquid supply tube 18 is connected to the lumens 1b and 1c so as to supply the fluid to the lumens 1b and 1c of the probe 1. The other end of the liquid supply tube 18 is connected to the reservoir 5 through the quantitative discharge pump 4. The reservoir 5 stores a gene dispersion, i.e., the dispersion in which a gene is dispersed in an ionic solution of the physiological condition, or an ionic solution in which a gene-packaging particle is dispersed.

The third tube extending from the branching portion 15 is a 2-core a 2-conductor signal cable 21. Cores 21a and 21b of the signal cable 21 extend through the lumens 1b and 1c of the probe 1 and are electrically connected to the needle cannulas 8a and 9a. The other end of the signal cable 21 is connected to the high-voltage pulse source 7. Reference numeral 12 denotes a light source and video-processing apparatus for endoscopic observation.

The operation of the apparatus for gene therapy having the above arrangement will be described below.

After the probe 1 is inserted into the instrument channel 3 of the angio-endoscope 2 which has been inserted into the blood vessel A, the syringe 17 is operated to supply air to the balloon 10 through the lumen 1a. The balloon 10 is inflated to separate the catheters 8 and 9 in a fork-like shape shown in FIG. 1. When the angio-endoscope 2 is moved forward or the like, the inner wall portions of the blood vessel A are transfixed with the needle cannulas 8a and 9a. In this state, the quantitative discharge pump 4 is operated to supply the gene dispersion stored in the reservoir 5 through the liquid supply tube 18 and the lumens 1b and 1c by an amount indicated from the setting unit 6. The gene dispersion is injected into the tissue in the inner wall of the blood vessel through the needle cannulas 8a and 9a. As shown in FIGS. 5(a) and 5(b), a large number of genes 24 for treatment are present around a cell 25 in the tissue injected with the gene dispersion.

The high-voltage pulse source 7 is turned on to apply a pulse voltage to the needle cannulas 8a and 9a through the cores 21a and 21b of the signal cable 21. The cell is set in a state shown in FIG. 5(a) prior to application of the pulse voltage. However, when the pulse voltage is applied, the cell membrane is instantaneously evaporated by the energy of the pulse current, so that small pores 25a and 25b are formed in the cell, as shown in FIG. 5(b). The genes 24 for treatment present around the cell 25 are transferred into the cell through the pores 25a and 25b without requiring the cellular physiological function. The cell incorporating the genes 24 for treatment recovers the normal function or obtains a desired function by expression of an enzyme protein encoded by the gene for treatment. Note that the pores 25a and 25b formed in the cell membrane are closed by the self-recovery action of the cell membrane.

In the apparatus for gene therapy according to this embodiment, the gene for treatment can be transferred into the cell at the target portion with a high probability within a short period of time. In addition, the types of target cells are not limited to a specific one in order to obtain the above effect.

FIG. 6 shows an apparatus for gene therapy according to the second embodiment of the present invention. This embodiment employs a mechanical pore formation system.

Referring to FIG. 6, reference numeral 81 denotes a probe. The probe 81 has a double lumen structure. An actuator unit 83 is incorporated in the distal end portion of a first lumen 82. One end of a liquid supply tube 85 is connected to a second lumen 84 to supply a liquid to the lumen 84. The other end of the liquid supply tube 85 is connected to a reservoir 87 through a quantitative discharge pump 86. A setting unit 88 is electrically connected to the quantitative discharge pump 86.

The actuator unit 83 is arranged such that a stacked piezoelectric element 90 is incorporated in a cylindrical metal pipe 89. The stacked piezoelectric element 90 is connected to a stacked piezoelectric element control unit 91. The stacked piezoelectric element 90 has two end faces perpendicular to its extendible direction. One end face is fixed to a partition wall 92 in the cylindrical metal pipe 89. A multi-needle member 93 (each cannula has an outer diameter of about 1 μm) manufactured by etch-processing of silicon is fixed to the other end face. Lead wires 94 for the stacked piezoelectric element 90 are electrically connected to the stacked piezoelectric element control unit 91. The lead wires 94 are soldered to the stacked piezoelectric element 90. This soldering portion is electrically insulated by a means such as an insulating resin coat. The distal end of the multi-needle member 93 is located inside the cylindrical metal pipe 89 when the stacked piezoelectric element 90 contracts. However, when the stacked piezoelectric element 90 is extended, the distal end of the multi-cannula member 93 appears outside the cylindrical metal pipe 89.

In use of the apparatus for gene therapy according to this embodiment, a predetermined amount of a gene dispersion in the reservoir 87 is sprayed on a target portion of a living body through the second lumen 84. The distal end portion of the probe 81 is brought into tight contact with the target portion of the living body, and the stacked piezoelectric element 90 is then extended to transfix the human living cell with the needles of the multi-needle member 93, thereby forming small pores in the surface of the cell. Thereafter, when the stacked piezoelectric element 90 is caused to contract and is moved away from the cell, the sprayed gene is transferred into the cell through the pores.

FIG. 7 shows an apparatus for gene therapy according to the third embodiment. This embodiment exemplifies an arrangement obtained by combining the electrical pore formation system of the first embodiment with the multi-needle structure similar to the second embodiment.

Referring to FIG. 7, reference numeral 101 denotes a catheter. A Pt endoelectrode 102 of multi-needle structure is mounted on the distal end of the catheter 101. Lead wires 103 are connected to the Pt endoelectrode 102. The lead wires extend through the interior of the catheter 101 and are connected to an external electrode 105 through a pulse source (several kV/200 ms) 104. Although not shown, a means for supplying a gene dispersion to the tissue is arranged in the catheter 101 in the same manner as described with reference to the first and second embodiments. Preferably, a means for needling the Pt electrode into the tissue is preferably as in the second embodiment (FIG. 6).

In use of the apparatus according to the third embodiment, the catheter 101 is inserted into a body cavity to supply the gene dispersion to a tissue 106 of the predetermined portion. The Pt electrode 102 is needled into the tissue 106, and the external electrode 105 is brought into contact with a predetermined body surface. A pulse voltage is applied across the endoelectrode 102 and the external electrode 105. In the same manner as described with reference to the first embodiment, pores are formed in the surface of the cell located between the endoelectrode 102 and the external electrode 105, so that the gene supplied to the tissue beforehand is incorporated in the cell through the pores.

FIG. 8 shows an apparatus for gene therapy according to the fourth embodiment. This embodiment is a modification of the third embodiment.

Referring to FIG. 8, reference numeral 101 denotes a catheter; 102, an endoelectrode; 103, lead wires; and 106, a living body tissue. This embodiment does not employ any external electrode, but the endoelectrode 102 is arranged as follows instead. More specifically, the endoelectrode 102 comprises a ceramic substrate 107 and a plurality of electrode rods 108 embedded in the ceramic substrate 107. The electrode rods 108 are sintered together with the ceramic substrate 107. The proximal end portions of the electrode rods are connected to the lead wires 103, respectively. The distal end portion of each electrode rod 108 has a conical, needle-like shape, and the surface of the distal end is covered with a Pt plating layer 109. The pitch between the distal ends of the electrode rods 108 is 0.5 mm. Reference numeral 110 denotes an insulating coating layer formed using, e.g., parylene(poly-para-xylylene). In this arrangement, the electrodes 108 are electrically insulated from each other, and pulse voltages (200 V/200 ms) having opposite polarities are applied to the adjacent electrode rods 108. Note that other arrangements of this embodiment are the same as those of the third embodiment shown in FIG. 7.

In the above arrangement, after the endoelectrode 102 is needled into the tissue 106, positive (+) and negative (−) pulse voltages are alternately applied to the electrode rods 108. The pores are formed in the surfaces of the cells located between the electrode rods, and the gene supplied beforehand is transferred to the cells through the pores.

FIG. 9 shows the overall arrangement of an apparatus for gene therapy using a laser pore formation system according to the fifth embodiment of the present invention. Referring to FIG. 9, reference numeral 31 denotes a probe. The probe 31 has a structure in which an optical fiber bundle 32 is parallel to a lumen 33.

The proximal end portion of the optical fiber bundle 32 is connected to a laser optical system 37, and the optical system 37 comprises a pulse laser source 34, a half mirror 35, and a condenser lens 36. Convex lens surfaces 32a are respectively formed on the exit end faces of the fibers constituting the optical fiber bundle 32. Each fiber has a one-to-one correspondence with the half mirror 35 and the condenser lens 36. These optical elements are optically arranged such that light emitted from the pulse laser source 34 is entered into each fiber through the half mirror 35 and the condenser lens 36. Note that the pulse laser source 34 is a short-wavelength laser having a wavelength which is ⅓ (355 nm) that of a Q-switched Nd-YAG laser.

The convex lens surfaces 32a of the optical fiber bundle 32 are formed as follows. A glass plate having characteristics suitable for a lens is fixed on the end face of the optical fiber bundle 32. A photosensitive film (e.g., methyl polymethacrylate) is applied to the surface of the glass plate, portions corresponding to the end faces of the individual optical fibers are selectively exposed. When etching is then performed, a nonexposed portion is etched faster, thereby obtaining the lens surfaces 32a shown in FIG. 9.

On the other hand, the proximal end portion of the lumen 33 is connected to a liquid supply system 42. The liquid supply system comprises a liquid supply tube 38, a quantitative discharge pump 39, a reservoir 40, and a setting unit 41. The lumen 33 is open at the distal end of the probe 31.

In gene therapy using the apparatus of the embodiment shown in FIG. 9, the quantitative discharge pump 39 is operated to supply a gene dispersion having a predetermined amount from the reservoir 40 to the lumen 33 through the fluid supply tube 38. The gene dispersion supplied to the lumen 33 is discharged from the distal end opening of the lumen 33 and is sprayed on the target portion of the living body. Thereafter, when a pulse laser is emitted from the pulse laser source 34, the pulse laser is optically transmitted through the half mirror 35, the condenser lens 36, and the optical fiber bundle 32 and emitted from the exit end face of the optical fiber bundle 32. At this time, since the convex lens surfaces 32a are formed on the exit end faces of the fibers constituting the optical fiber bundle 32, the pulse laser is focused by the lens surface 32a and is radiated on a human living cell. The cell membrane is instantaneously evaporated upon radiation of the focused pulse laser, thereby forming pores in the cell membranes. The gene sprayed beforehand is incorporated in the cell through each pore. As a result, the same effect as in the first embodiment shown in FIG. 1 is obtained. It should be noted that when the energy of the laser beam is excessively high, the protoplasm is also evaporated in addition to the cell membrane, thereby killing the cell. However, it is possible to form pores in only the cell membrane by appropriately determining the energy of the laser beam, using an appropriate means such as formation of an aperture in the laser source 34.

In this case, a laser beam can be focused to 1 μm or less by forming the convex lens surfaces 32a, and the focused laser spot can be formed on the cell, so that the size of the pore formed in the surface of the cell is very small, thereby preventing the cell from invasion and increasing the survival rate of the gene-transfected cells. To the contrary, in the absence of the convex lens surfaces 32, the size of the laser beam to be radiated on the cell is increased by several μm, and the size of the pore formed in the cell is increased. Therefore, the survival rate of the gene-transfected cells is decreased.

FIG. 10 shows the sixth embodiment. This embodiment is a modification of the fifth embodiment described above. The sixth embodiment includes another means for radiating a laser beam emitted from the optical fiber bundle 32 on a sufficiently narrow region.

Referring to FIG. 10, reference numeral 111 denotes a probe. An optical fiber bundle 112 is inserted through one of the lumens formed in the probe 111. A distal-end chip 113 made of ceramics which does not transmit a laser beam therethrough is formed at the exit end face of the optical fiber bundle 112. The distal-end chip is obtained by forming a large number of through holes each having a diameter of about 0.1 μm in a glass-like ceramic plate. The ceramic plate having a large number of through holes can be formed by a known LIGA process. The term "LIGA" stands for Lithografie (German word which means lithography) Galvanoformung (German word which means electroplating) and Abformung (German word which means molding). This LIGA process is a technique for forming a micropatterned structure having a high aspect ratio in accordance with deep lithography using an X-ray and electroplating. The details of the LIGA process are described in, e.g., "Product Miniaturization by Micromachine Technique", Chinoka Jiten, Ed. Kabushiki Kaisha Sangyo Chosakai Jiten Shuppan Center, PP. 41–45.

Figure 11:
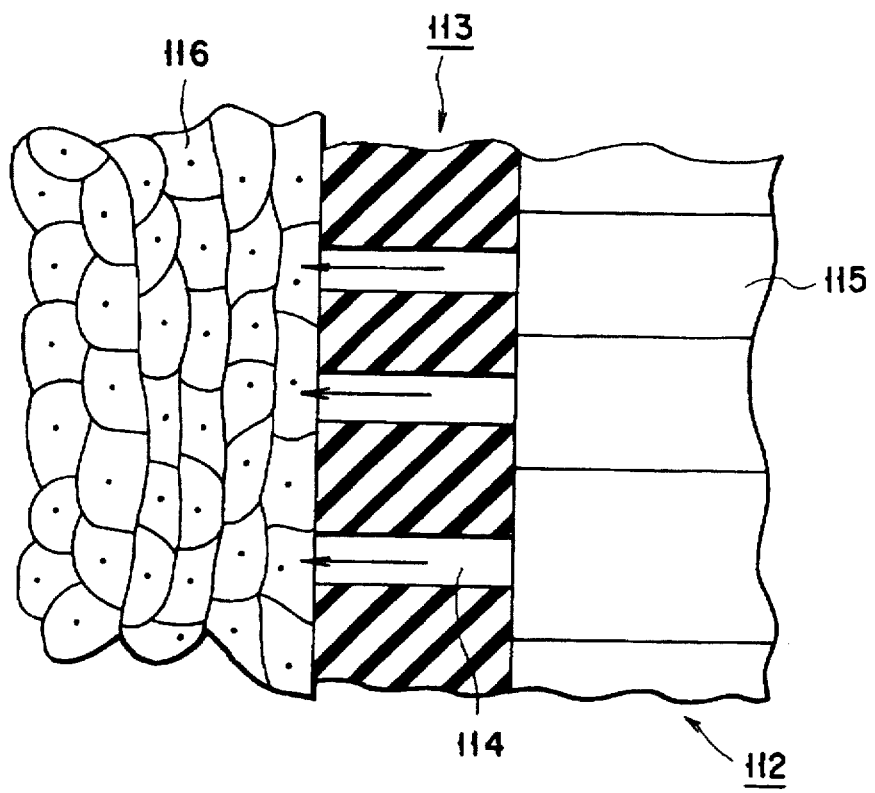
FIG. 11 is a view for explaining the operation of the apparatus for gene therapy of the embodiment shown in FIG. 10.

FIG. 11 is an enlarged view of the distal-end chip 113. Referring to FIG. 11, reference numerals 114 denote through holes formed in the distal-end chip 113; and 115, individual optical fibers constituting the optical fiber bundle 112. Reference numerals 116 denote individual cells constituting the tissue. As shown in FIG. 11, the through holes 114 are formed in a one-to-one correspondence with the individual optical fibers 115. The diameter (about 0.1 μm) of the through hole 114 is much smaller than the size of each cell 116. As indicated by arrows in FIG. 11, laser beams are radiated on the cells 116 through the through holes 114, respectively. The pore formed in the surface of each cell is very small, and the survival rate of the gene-transfected cells can be increased. In this embodiment, although the diameter of the through hole 114 is set to be about 0.1 μm, its size can be appropriately determined in accordance with the size of a target tissue cell.

Figure 12:
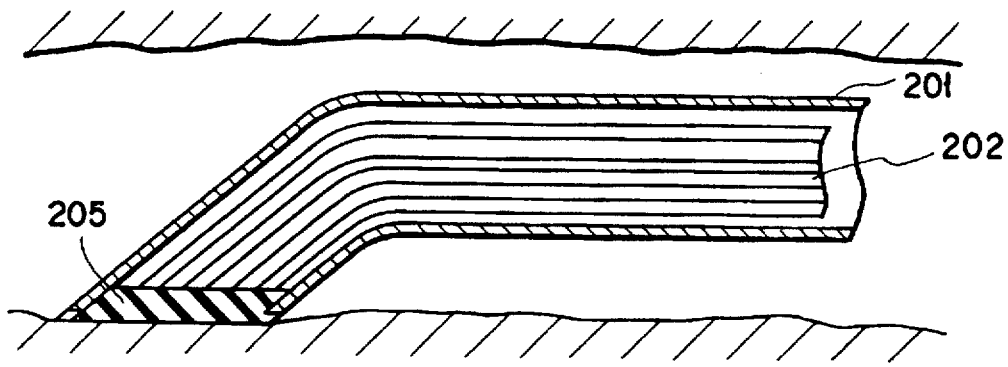
FIGS. 12 to 14 are views showing an apparatus for gene therapy according to the seventh embodiment of the present invention.
Figure 13:
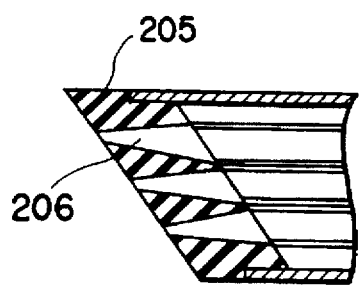
Figure 14:
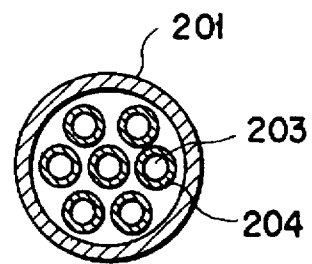

FIGS. 12 to 14 show the seventh embodiment. This embodiment is a modification of the sixth embodiment shown in FIG. 10. The characteristic feature of the seventh embodiment lies in that a laser beam can radiated on the inner wall of a blood vessel into which the probe is inserted. FIG. 12 is a view showing a state in which the probe is inserted into the blood vessel, FIG. 13 is a view showing the distal end portion of the probe, and FIG. 14 is a cross-sectional view of the probe.

In this embodiment, a metal jacket 201 having a bent distal end portion is used as a guide for the optical fiber bundle. The openings at the distal end portion of the metal jacket 201 are tapered toward the distal end, as shown in FIG. 13, so that the openings can face the blood vessel wall when the probe is inserted into the blood vessel. An optical fiber bundle 202 is inserted in the metal jacket 201. Each optical fiber constituting the optical fiber bundle 202 comprises a core 203 and a cladding layer 204 which surrounds the core 203, as shown in FIG. 14. A ceramic distal-end chip 205 is mounted on the opening of the distal end of the metal jacket 201 in the same manner as in the embodiment shown in FIGS. 10 and 11. As shown in FIG. 13, the distal-end chip 205 has an opening 206 slightly larger than the size of the core 203. The diameter of each opening is gradually tapered toward the exit end.

In gene therapy using the apparatus of this embodiment, the metal jacket is inserted into the blood vessel. When the distal end of the metal jacket reaches a predetermined portion, a gene suspension is injected through the hollow portion of the probe 121. The optical fiber bundle 202 is inserted into the hollow portion of the probe 121, and the distal end of the probe 121 is located in the state shown in FIG. 12. A pulse laser having a predetermined energy is supplied through the optical fiber bundle 202, and the beams are radiated from the openings 206 of the distal-end chip 205 on the inner wall surface of the blood vessel. Therefore, the pores are formed in the cell membrane of the cell of the blood vessel, and the gene injected beforehand is transferred to the cell.

Figure 15:
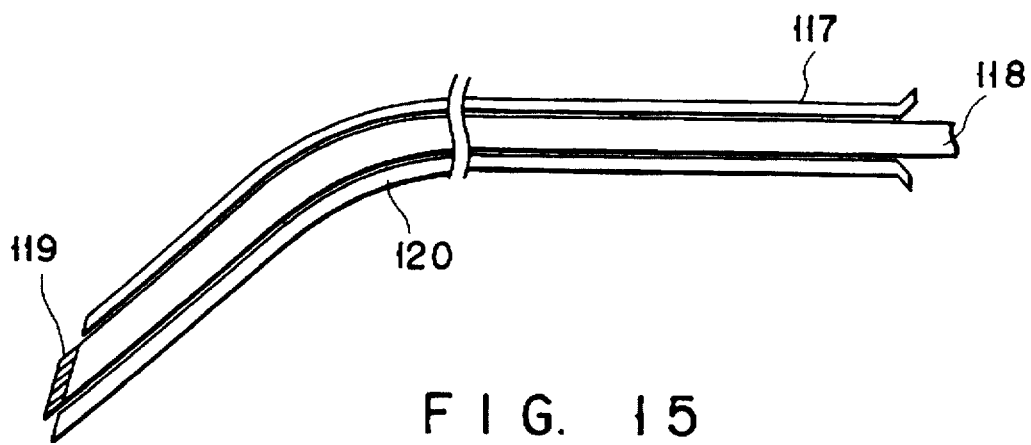
FIG. 15 is a view showing an apparatus for gene therapy according to the eighth embodiment of the present invention.

FIG. 15 shows the eighth embodiment. The characteristic feature of this embodiment also lies in that a predetermined flexible bent portion is formed near the distal end of a probe.

Referring to FIG. 15, reference numeral 117 denotes a probe consisting of a hollow optical fiber. The outer diameter of the probe 117 is 0.3 mm, and an optical fiber bundle 118 constituted by several tens of optical fibers can be inserted into the hollow portion of the probe 117. The distal end faces of the probe 117 and the optical fiber bundle 118 are tapered, so that the distal ends are pointed. A distal-end chip 119 as in the embodiment of FIG. 10 is mounted on the exit end face of the optical fiber bundle 118. A predetermined bent portion 120 (FIG. 15) is formed near the distal end of the probe 117.

The embodiment shown in FIG. 15 provides the following specific function.

Figure 16:
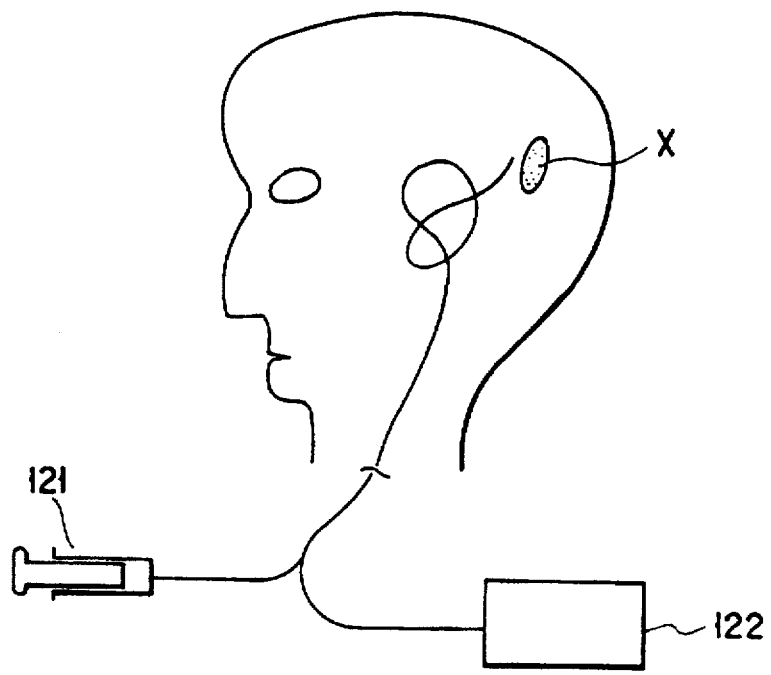
FIG. 16 is a view for explaining the operation of the apparatus for gene therapy of the embodiment in FIG. 15.

Since the hollow optical fibers constituting the probe 117 have a large elastic force and a large torque transmission value, when the probe 117 is inserted into a blood vessel, the insertion direction of the distal end can be controlled upon manual operations such as rotation, pushing, and pulling. In addition, since the optical fiber is made of glass active in terms of proton NMR, the distal end of the probe inserted into the blood vessel can be observed with an MRI technique. For example, as shown in FIG. 16, the probe 117 is suitable for gene therapy for inserting the probe in a complicated blood vessel system in a brain. More specifically, the probe 117 is inserted into a blood vessel while the movement of the probe 117 is being observed with an MRI technique. The distal end of the probe 117 inserted into the blood vessel under NMR observation. At a blood vessel branching portion, the probe 117 is manipulated to be rotated, pulled, or pushed to select a desired branched vessel. The distal end of the probe 117 can thus reach a morbid portion X. When the distal end of the probe 117 reaches the morbid portion X, a gene suspension is injected from a syringe 121 to the morbid portion X through the hollow portion of the probe 117. The optical fiber bundle 118 is then inserted into the hollow portion of the probe 117, and the distal end of the optical fiber bundle 118 is placed to the morbid portion X. A pulse laser beam (e.g., a wave having an energy three times that of Q switch) is supplied from a pulse laser source 122 to the optical fiber bundle 118 and is radiated from the distal-end chip 119 of the distal end of the probe 117 to the morbid cell. A pore is formed in the cell membrane of the morbid cell, and the gene injected beforehand is transferred into the cell.

According to the apparatus for gene therapy of this embodiment, since a treatment can be performed under the MRI observation, a gene can be properly transferred into a morbid portion exhibiting an abnormality in oxygen metabolism, which portion cannot be observed with X-ray CT.

Figure 17:
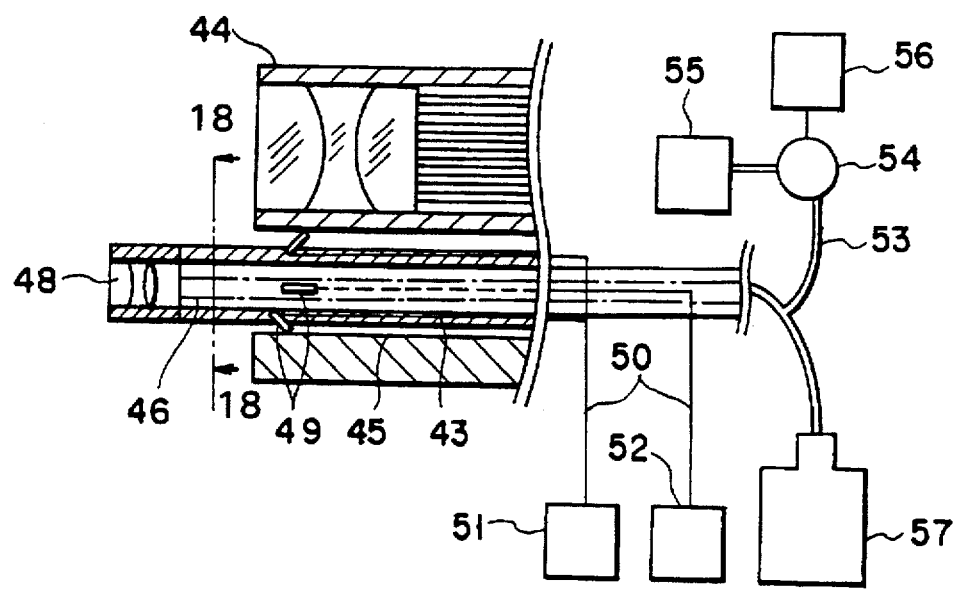
FIG. 17 is a view showing the overall arrangement of an apparatus for gene therapy according to the ninth embodiment of the present invention.
Figure 18:
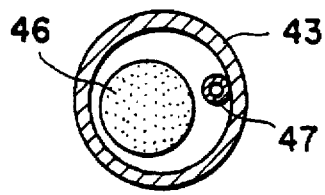
FIG. 18 is a cross-sectional view of the apparatus along the line 18—18 of FIG. 17.

FIGS. 17 and 18 show an apparatus for gene therapy according to the ninth embodiment of the present invention. This embodiment also employs a laser pore formation system.

Referring to FIGS. 17 and 18, reference numeral 43 denotes a probe. As shown in FIG. 17, the probe 43 is inserted in an instrument channel 45 of an endoscope 44 to be used. An optical fiber bundle 46 and a lumen 47 are inserted in the probe 43 in a parallel manner, as shown in FIG. 18. In addition, as shown in FIG. 17, a condenser lens 48 is mounted on the distal end of the probe to oppose the end face of the optical fiber bundle 46.

Four thin rectangular projections 49 each made of PVDF (a polyvinylidene fluoride having a piezoelectric property) extend on the outer circumferential surface near the distal end portion of the probe 43 along the circumferential direction. Two lead wires 50 corresponding to each of the projections 49 are embedded in the wall portion of the probe 43 to be parallel to the longitudinal direction of the probe. These lead wires 50 are electrically connected to the corresponding projection 49. All the lead wires 50 are connected to PVDF control units 51 and 52 so that the opposite two projections are paired. That is, the lead wires 50 connected to one pair consisting of two projections 49 are connected to the PVDF control unit 51 so that voltages having opposite polarities are applied to the two projections 49. The lead wires 50 connected to the other pair consisting of two projections 49 are connected to the PVDF control unit 52 so that voltages having opposite polarities are applied to the two projections 49.

On the other hand, a liquid supply tube 53 is connected to the proximal end portion of the lumen 47. The liquid supply tube 53 is connected through a quantitative discharge pump 54 to a reservoir 55 which stores a gene dispersion. A setting unit 56 is connected to the quantitative discharge pump 54. One end of the optical fiber bundle 46 opposes the condenser lens 48, and its other end is optically connected to a pulse laser unit 57.

The operation of the apparatus for gene therapy according to the embodiment shown in FIG. 17 will be described below.

The quantitative discharge pump 54 is operated to introduce the gene dispersion from the reservoir 55 to the lumen 47 through the liquid supply tube 53 by a predetermined amount indicted from the setting unit 56. The gene dispersion is discharged from the opening at the distal end of the lumen 47 and is sprayed on the target portion of a living body. A pulse laser beam having a predetermined cycle (e.g., 10 Hz) is emitted from the pulse laser unit 57. This laser beam is transmitted through the optical fiber bundle 46 and is focused by the condenser lens 48, thereby outputting the focused beam.

When sine waves are supplied from the PVDF control units 51 and 52 to the projections 49, the paired projections 49 are synchronously vibrated. Thus, at the outlet portion of the instrument channel 45, the distal end portion of the probe 43 is vibrated in the vertical and horizontal directions. Therefore, a laser beam focused by the lens 48 is sequentially radiated on a considerable number of cells present within the predetermined range, not limited to the cells present in one direction. Pores are formed in the surfaces of these cells. As a result, a large number of genes sprayed beforehand are incorporated in the large number of cells through the pores, thereby obtaining the same effect in each cell as described previously.

Figure 19:
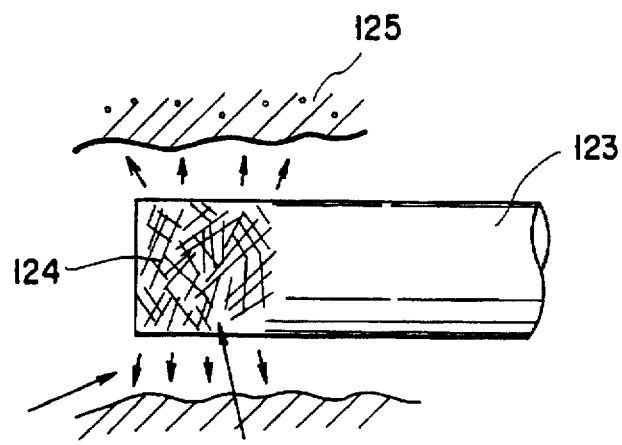
FIG. 19 is a view showing an apparatus for gene therapy according to the tenth embodiment of the present invention.
Figure 20:
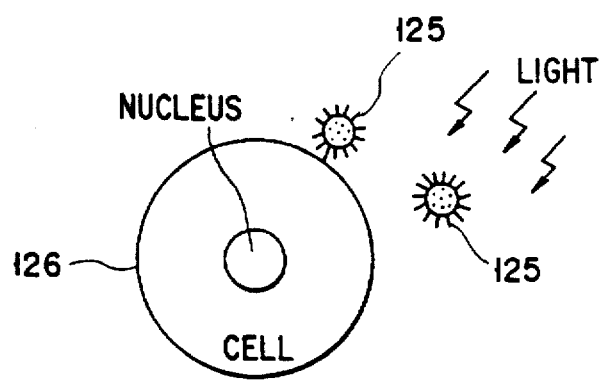
FIG. 20 is a view for explaining the operation of the apparatus for gene therapy of the embodiment shown in FIG. 19.

FIGS. 19 and 20 show an apparatus for gene therapy and a therapeutic method according to the tenth embodiment of the present invention. This embodiment also employs laser radiation. However, unlike the direct laser pore formation scheme of the above embodiment, an indirect laser pore formation system is employed in the tenth embodiment.

Referring to FIG. 19, reference numeral 123 denotes an optical fiber connected to a laser source. A rough surface region 124 is formed at the distal end portion (laser exit end face) of the optical fiber 123 by a means such as filing. A laser beam transmitted through the optical fiber emits from the rough surface region in all directions, as indicated by arrows in FIG. 19.

Laser beam absorption particles 125 coated with a gene to be transferred are used in gene transfection using the above apparatus. Each particle 125 is a particle such as a magnesium particle, a beryllium particle, or a barium particle which can absorb a laser beam and is not toxic to the cells. The laser beam absorption particles 125 coated with the gene for treatment are administered beforehand in a tissue such as the inner wall of a blood vessel by intravenous injection or local injection. In this state, the optical fiber 123 is inserted into a blood vessel, as shown in FIG. 19, to emit a laser beam. Unlike in the previous embodiments, the energy of the laser beam radiated in the blood vessel suffices if it can heat up the carrier particles 125 and need not be high enough to form pores in the cell membranes. As shown in FIG. 20, the laser beam transmitted in the tissue is absorbed by the particles 125 located around the cell, thereby heating the particles 125. The heated carrier particles are attached to the nearby cell and heat up small regions of the cell membrane of this cell to form pores in these regions. At the same time, the particles are incorporated in the cell through the pores. As a result, the gene for treatment is transferred into the cell together with the particles 125.

As described, a laser beam having a relatively low energy can be used in this embodiment to advantageously suppress damage to the tissue. Note that a hydrophobic functioned group may be coated on the surface of each carrier particle 125 so as to improve attachment of the carrier particles 125 onto a cell 126. In this case, the gene for treatment is not coated on the surface of the particle, but is used while the gene for treatment is free from the particle. For example, a suspension mixture in which the particles 125 and the gene for treatment are suspended may be administered in the tissue beforehand.

FIGS. 21 and 22 show an apparatus for gene therapy according to the eleventh embodiment of the present invention. This embodiment employs a gene gun system. A probe of this embodiment is used to be inserted into mainly an upper digestive tract and an abdominal cavity.

Referring to FIG. 21, reference numeral 61 denotes a gene gun probe. The probe 61 is connected to an $N_2$ gas bomb 63 through an air supply tube 62. The probe 61 is connected to a stacked piezoelectric element control unit 65 through lead wires 64. The probe 61 comprises a flexible tube 66 and a rigid distal end portion 67. A connecting portion between the flexible tube 66 and the rigid distal end portion 67 is covered with a metal pipe 68 and fixed by an adhesive.

The rigid distal end portion 67 has a partitioned structure comprising a first storage chamber 70 in which gene bullets 69 are stored and a second storage chamber 72 in which a stacked piezoelectric element 71 is arranged. Each gene bullet 69 is obtained by causing a gene to be adsorped onto the surface of a very small metal piece (size: about 1 fm; material: preferably gold). An opening 73 having a diameter of about 1/100 to 1/10 mm is formed at the distal end portion of the first storage chamber 70 which stores the gene bullets 69.

One end face of the stacked piezoelectric element 71, which is perpendicular to the extension direction thereof is in contact with a partition wall 74 for partitioning the first and second storage chambers 70 and 72. As shown in FIG. 22 as a cross-sectional view along the line C—C in FIG. 21, openings 75 are partially formed in the partition wall 74, and the stacked piezoelectric element 71 is arranged to mostly close the openings 75. The piezoelectric element 71, chamber 72, and the openings 75 in partition wall 74 comprise a transfer means for transfer of gas and gene bullets out of the apparatus. The other end face of the stacked piezoelectric element 71, which is perpendicular to the extension direction thereof is in contact with a partition wall 76 so as to close the opening formed in the partition wall 76 between the second storage chamber 72 and the flexible tube 66. In addition, through holes 77, 78, and 79 each having a diameter of a few submicrons to several μm are formed in the partition wall 76. The through holes 77 and 78 are formed to guide the lead wires 64 for the stacked piezoelectric element 71. After the lead wires 64 are inserted in the through holes 77 and 78, these holes are sealed with an epoxy resin or the like. The remaining hole 79 is left as it is.

In use of the apparatus for gene therapy according to this embodiment, the $N_2$ bomb 63 is opened, and the flexible tube 66 is maintained at an appropriate internal pressure. The $N_2$ gas flows into the second storage chamber 72 through the through hole 79 and then into the first storage chamber 70 through the opening 75 formed in the partition wall 74. The $N_2$ gas is then discharged outside through the opening 73. In this state, a small amount of $N_2$ gas flowing outside through the opening 73 is always present. Even if the apparatus is operated in a body cavity having a high humidity, moisture or a body fluid will not flow into the apparatus through the opening 73 due to the presence of this $N_2$ gas flow. Therefore, the gene bullets 69 can be prevented from being solidified and forming a clot by the absorption of the moisture.

A signal is output from the stacked piezoelectric element control unit 65 to cause the stacked piezoelectric element 71 to contract along the axial direction of the probe. The opening of the partition wall 76 and the opening 75 of the partition wall 74 are opened, and $N_2$ gas abruptly flows in the first storage chamber 70 through these openings and is sprayed outside through the opening 73. During abrupt spraying of the $N_2$ gas, the gene bullets 69 are abruptly sprayed and shot into the human living cells. Since the size of each gene bullet 69 is about 1 μm and is smaller than that (several tens of μm) of the human living cells, the pore formed in the cell membrane upon shooting of the gene bullet can be immediately restored. The shot gene bullet 69 is hydrated with $H_2O$ in the cell, and the gene is released from the carrier metal. The released gene exhibits a prescribed function. Since the carrier metal consists of a metal such as gold which is not toxic to the human body, the metal does not adversely affect the human body. When the stacked piezoelectric element 71 is returned to the initial state, the abrupt flow of $N_2$ gas is stopped, and spraying of the gene bullets 69 is stopped accordingly.

In the above embodiment, the gene bullet 69 obtained by adsorption of the gene on the very small metal piece of gold or the like is used. However, a compression-molded body of poly-L-lactic acid packaging a gene for treatment can be also used. Since polylactic acid is perfectly decomposed in the cell, it does not adversely affect the cell even if polylactic acid is transferred into the cell. Since the gene bullet using poly-L-lactic acid is excellent in moldability, a gene bullet having a desired shape can be advantageously obtained by compression molding. For example, when the gene bullet 69 is to be shot deeply, an elongated gene bullet 69a having a distal end of an acute angle can be formed, as shown in FIG. 23(A). However, when the gene bullet is to be shot shallowly, a gene bullet 69b having a distal end of a larger angle so as to increase the insertion resistance can be formed, as shown in FIG. 23(B).

The gene bullet consisting of poly-L-lactic acid can be manufactured by, for example, the following methods.

In the first method, poly-L-lactic acid is dissolved in an appropriate organic solvent mixture such as acetone/methylene chloride/chloroform, the resultant solution is mixed in a surfactant (aqueous PVA solution), and the resultant solution is stirred with an ultrasonic wave to form fine particles. These fine particles are drawn with a micropipet and are dripped in pyramidal micropatterned pores which are formed in an Si substrate by a micropatterning technique. When the organic solvent is evaporated, pyramidal polylactic acid bullets are formed. Thereafter, the gene is attached to the surface of the bullet, thereby obtaining a gene bullet.

In the second method, a gene suspension is formed by dispersing a gene in an aqueous solution. Poly-L-lactic acid is dissolved in an organic solvent to prepare a polylactic acid solution independently of preparation of the above gene suspension. The gene suspension and the polylactic acid solution are mixed in a surfactant under stirring with an ultrasonic wave. These starting materials are then emulsified to form poly-L-lactic acid particles each having a WOW (water/oil/water) interface structure and packages the gene therein. The resultant particles are molded in a pyramidal shape in the same manner as in the first method. By this method, a small gene bullet having a bottom surface with a diameter of 1 μm and a height of about 1 μm can be manufactured.

Figure 24:
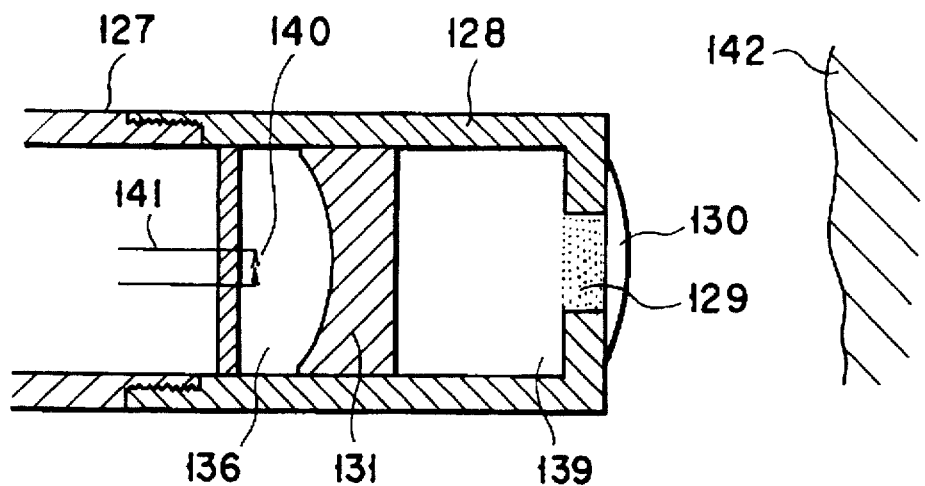
FIG. 24 is a view showing an apparatus for gene therapy according to the twelfth embodiment of the present invention.

FIG. 24 shows an apparatus for gene therapy according to the twelfth embodiment of the present invention. This embodiment also employs a gene gun system. A gene bullet injection mechanism is different from that of the eleventh embodiment. This gene gun is similarly inserted and used in an upper digestive tract and an abdominal cavity.

Referring to FIG. 24, reference numeral 127 denotes a gene gun type probe. An injection cylinder 128 made of metal is arranged at the distal end of the probe 127. An opening is formed at the distal end face of the cylinder 128, and gene bullets 129 described with reference to the previous embodiment are filled in the opening. The outer side of the opening is sealed with a polyurethane film 130. A slidable piston 131 is disposed inside the injection cylinder 128 so as to be movable along the inner wall of the cylinder 128. The interior of the cylinder 128 is divided into two chambers by the piston 131. The chamber at the left of the piston is an expansion chamber 136, and the chamber at the right of the piston is a compression chamber 139. A sparking element 140 is disposed inside the expansion chamber 136 and is connected to a power supply and a switch through lead wires 141 passing through the probe 127. An explosive compound such as lead azide ($PbZ_2$) or water is stored in the expansion chamber 136. $N_2$ gas or air having a predetermined pressure is sealed in the compression chamber 139.

The gene gun having the above arrangement shoots the gene bullets 129 in a tissue 142 of a patient in accordance with the following operation. That is, when spark discharge is generated, the explosive compound stored in the expansion chamber 136 explores or water stored in the expansion chamber 136 is evaporated to greatly increase the pressure of the expansion chamber. The piston 131 is moved to the right by the increased pressure to compress $N_2$ or air in the compression chamber 139, thereby greatly increasing the pressure of $N_2$ or air. As a result, the gene bullets 129 tear the polyurethane film 130 and are injected forward. The injected gene bullets 129 are shot into the tissue 142. The polyurethane film 130 serves as a waterproof film for blocking the moisture or body fluid in the body cavity and preventing the gene bullets 129 from absorbing the moisture and becoming viscous.

Unlike the gene gun of FIG. 21, since the gene gun of FIG. 24 does not require any $N_2$ bomb for injecting the gene bullets, the overall system can be made compact. In addition, a high pressure is imposed on only the cylinder portion at the distal end portion of the probe. That is, high-pressure $N_2$ gas filled in the gene gun of FIG. 21 need not be filled in the apparatus of this embodiment, so that the structure can be simplified.

Figure 25:
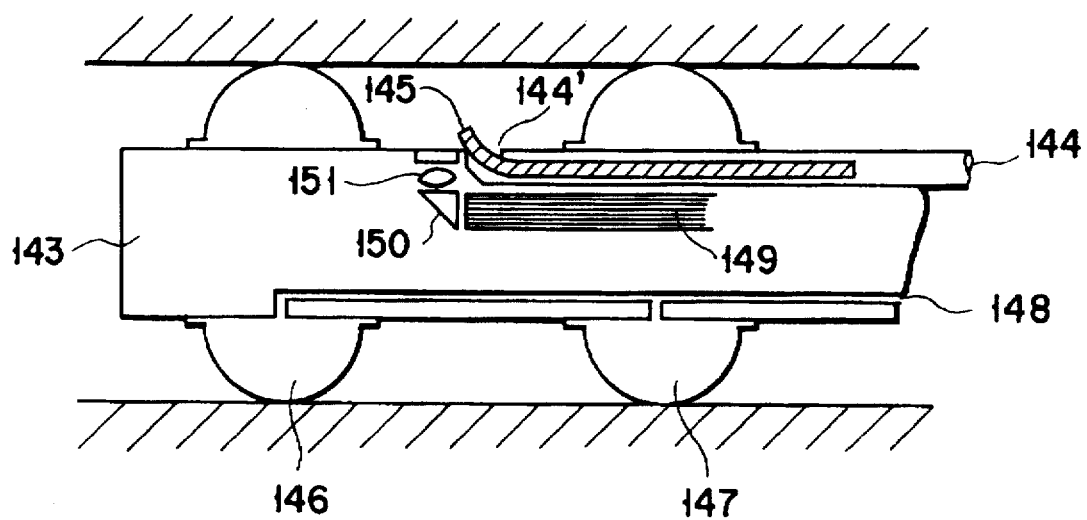
FIG. 25 is a view showing an apparatus for gene therapy according to the thirteenth embodiment of the present invention.

FIG. 25 shows an apparatus for gene therapy according to the thirteenth embodiment of the present invention. This embodiment aims at improving the gene gun in FIG. 21 or 24. That is, since the shot gene bullets receive a large resistance from a body fluid in a body cavity (e.g., a blood vessel or lymphatic vessel filled with the body fluid), it is difficult to shoot the gene bullets in the tissue. This embodiment exemplifies an apparatus including a gene gun capable of shooting gene bullets in the body cavity filled with a body fluid.

Referring to FIG. 25, reference numeral 143 denotes a catheter. This catheter 143 has a liquid channel 144. The liquid channel 144 has an opening 144' in the side wall of the distal end portion of the catheter. A gene gun 145 is inserted through the liquid channel 144. The distal end of the gene gun 145 is directed toward the inner wall of the blood vessel. The gene gun 145 may be the gene gun shown in FIG. 21 or 24. Two balloons 146 and 147 are arranged on the side wall of the distal end portion of the catheter 143 so as to interpose the opening 144'. An air channel 148 communicating with the balloons 146 and 147 is formed in the catheter 143. An optical system constituted by an optical fiber bundle 149, a prism 150, and a condenser lens 151 is arranged in the catheter 143 to radiate a laser beam.

In gene therapy using the above apparatus, the distal end portion of the catheter 143 is inserted up to a predetermined portion in a blood vessel while the gene gun 145 is not inserted and the two balloons 146 and 147 are deflated. Air or the like is supplied to the balloons 146 and 147 through the air channel 148 to inflate the balloons 146 and 147, thereby blocking the blood flow in the blood vessel. The blood is drawn through the liquid channel 144 so that no blood is present between the two balloons 146 and 147. In this state, the gene gun 145 is inserted into the channel 144, as shown in FIG. 25, and the gene bullets are injected toward the wall of the blood vessel in the same manner as described with reference to the previous embodiment. The injected gene bullets are properly shot into the tissue without receiving the blood resistance. At this time, laser beam radiation may also be used. The subsequent effect is the same as that of the previously described embodiments.

Figure 26:
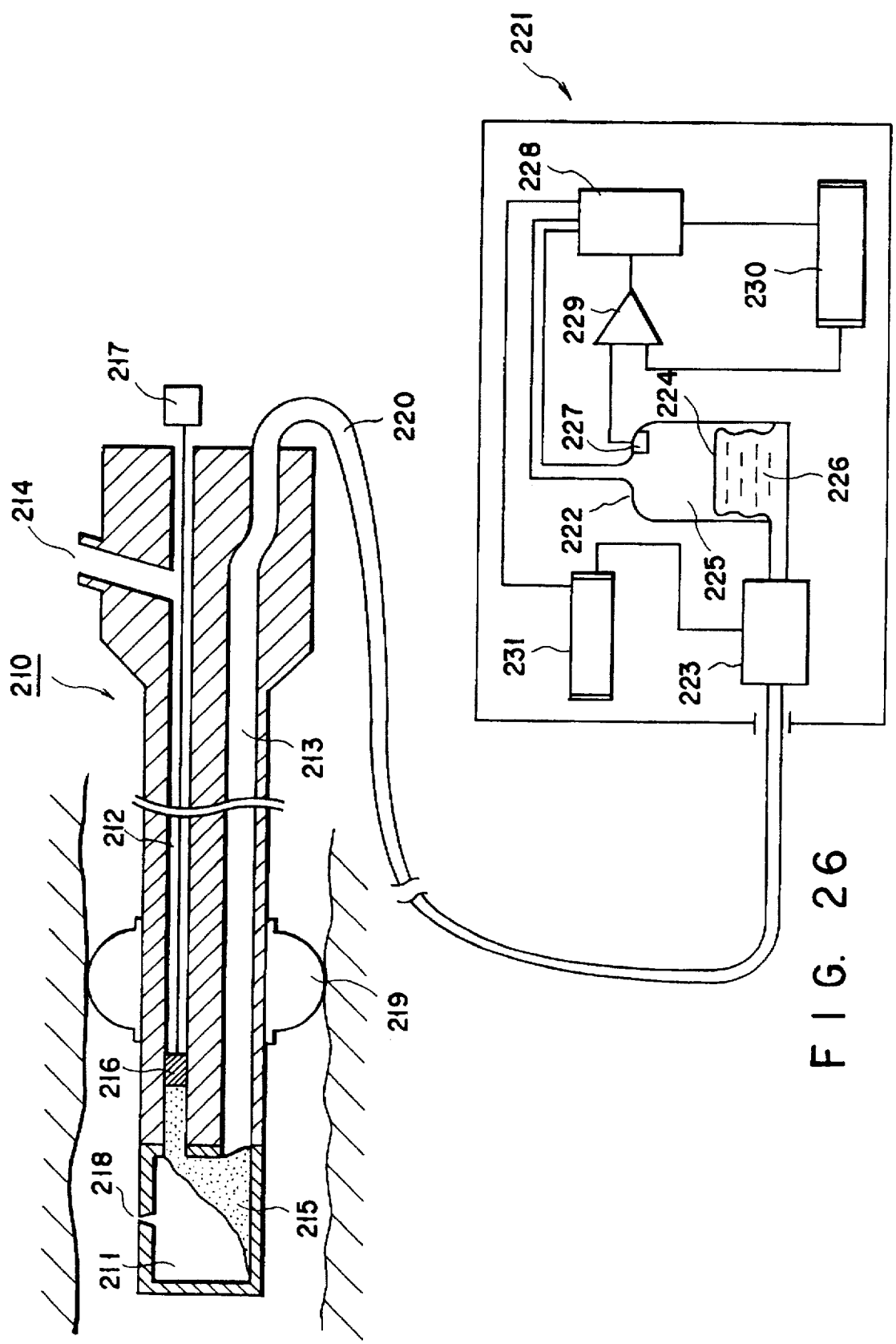
FIG. 26 is a view showing an apparatus for gene therapy according to the fourteenth embodiment of the present invention.

FIG. 26 shows an apparatus for gene therapy according to the fourteenth embodiment of the present invention. This embodiment also employs a gene gun system, but is different from the previous embodiments in that a means for shooting a gene bullet is a high-pressure liquid (e.g., physiological saline), and that a means for loading gene bullets is arranged.

Referring to FIG. 26, reference numeral 210 denotes a gene gun probe. A gene bullet storage chamber 211 is formed at the distal end portion of the probe 210. A gene bullet supply channel 212 and a liquid supply channel 213 are formed communicated by with the storage chamber 211. A gene filling port 214 to the gene supply channel 212 is formed. Gene bullets 215 filled from the gene filling port 214 are conveyed to the storage chamber 211 by a bullet loading tool 217 having a distal-end chip 216. When the gene bullets 215 are completely filled, the loading tool 217 is fixed to the probe 210 in this state, and the distal-end chip 216 serves as a liquid-tight packing. Upon completion of bullet loading, for example, physiological saline is supplied through the liquid supply channel 213 at a high pressure. This physiological saline flows in the gene storage chamber 211 and is injected together with the gene bullets 215 from an injection port 218 to the wall of the blood vessel. The gene bullets 215 are shot into human living cells. Note that a balloon 219 having the same structure as that described with reference to the embodiment of FIG. 25 is formed on the side wall of the probe 210 to stop the blood flow.

The liquid supply channel 213 is connected to a liquid supply unit 221 through a supply tube 220. The liquid supply unit 221 comprises a supply tank 222. The supply tank 222 is connected to the supply tube 220 through a control valve 223. The supply tank 222 is partitioned into a compression chamber 225 and a storage chamber 226 by an extendible partitioning member 224. The storage chamber 226 stores physiological saline. The compression chamber 225 has a pressure sensor 227 and is connected to a compression pump 228. The pressure sensor 227 is connected to a setting unit 230 through a comparator 229. A predetermined pressure can be automatically or manually set at the setting unit 230. When a main switch 231 is turned on, the control valve 223 is opened in accordance with a signal from the main switch 231. At the same time, the compression pump 228 is operated. Upon operation of the compression pump 228, the partitioning member 224 is pressed downward to compress the storage chamber 226. As a result, the physiological saline stored in the storage chamber 226 is compressed, and the compressed physiological saline is supplied to the liquid supply channel 213 through the supply tube 220. A pressure signal output from the pressure sensor 227 is input to the comparator 229 and is compared with a signal from the setting unit 230. The comparator 229 controls the pressure of the compression pump 228 in accordance with the comparison result. Therefore, the physiological saline can always be supplied at a predetermined pressure.

In this embodiment, the gene bullets 215 are shot from the side wall of the probe 210. The gene bullets can be transferred in a cell of the wall of a blood vessel even if the cavity is narrow as in a blood vessel. In addition, since the gene bullets can be filled from the operating end portion of the probe, the probe need not be removed for bullet loading, and repeated treatment can be performed.

Figure 27:
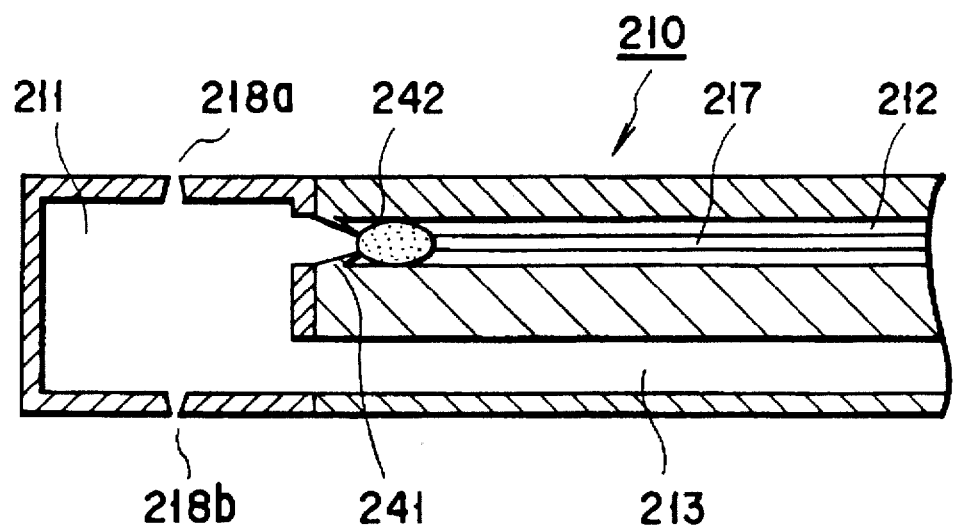
FIG. 27 is a view showing an apparatus for gene therapy according to the fifteenth embodiment of the present invention.

FIG. 27 shows the fifteenth embodiment of the present invention. This embodiment is a modification of the embodiment shown in FIG. 26. The same reference numerals as in FIG. 26 denote the same parts in FIG. 27, and a detailed description thereof will be omitted. According to the first characteristic feature of this embodiment, two injection ports 218a and 218b are formed in side surface portions of a gene storage chamber 211. The second characteristic feature lies in a bullet loading means. That is, projections 241 are formed near the outlet of a gene bullet supply channel 212. A bag 242 filled with gene bullets is mounted at the distal end of a bullet loading tool 217. When the bullet loading tool 217 is inserted, the bag 242 is pierced and torn by the projections 241. As a result, the gene bullets filled in the bag 242 are discharged from the bag. The gene bullets are then stored in the storage chamber 211. Other arrangements of this embodiment are the same as those of FIG. 26.

In this embodiment, since the plurality of injection ports 218a and 218b are formed in the side surface of the gene storage chamber 211, the gene bullets can be transferred in a wide range of a vessel tissue. The gene can be easily transferred to a morbid portion without considering the directivity of the probe.

Unlike in the above embodiments, the following embodiment does not transfer a gene into cells by forming a pore in a cell membrane. Instead, gene transfection depending on cellular physiology is utilized effectively and efficiently.

Figure 28:
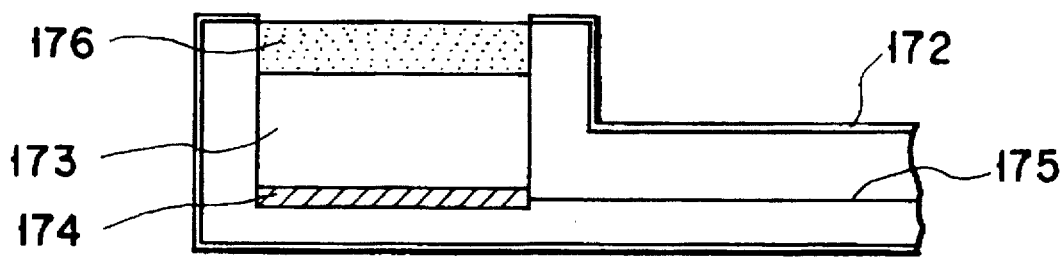
FIG. 28 is a view showing an apparatus for gene therapy according to the sixteenth embodiment of the present invention.

FIG. 28 shows an apparatus for gene therapy according to the sixteenth embodiment of the present invention. According to this embodiment, a gene for treatment sprayed in the wall of a body cavity is administered deep inside the tissue in accordance with electrophoresis.

Referring to FIG. 28, reference numeral 172 denotes a probe for gene therapy. A gene storage chamber 173 is formed at the distal end of the probe 172. A gene suspension in which a gene for treatment is suspended is filled inside the gene storage chamber 173. A Pt electrode 174 is arranged on the bottom surface of the gene storage chamber 173 to cause electrophoresis of the gene for treatment. This Pt electrode is connected to a voltage supply (not shown) through a lead wire 175. An opening is formed in the upper portion of the gene storage chamber 173. This opening is closed with a semipermeable film 176 having pores allowing permeation of the gene. A substance such as $^{11}$C-N-methylspiperon which can be detected by a positron emission computer tomographic imaging apparatus (PET) is coated on the outer surfaces of the probe 172 and the gene storage chamber 173.

FIG. 29 shows an application of gene therapy using the apparatus of this embodiment. Two probes 172 are respectively inserted into an arachinoidal cavity or the peripheral portion of the brain cavity through channels of endoscopes 177. The positions of the distal end portions of the probes 172 are monitored with a PET (not shown). The gene storage chamber 173 and another gene storage chamber 173' are arranged so that a morbid portion is interposed between the two Pt electrodes 174. A predetermined voltage is applied across the two Pt electrodes 174 by an electrophoresis unit 178. The genes for treatment stored in the gene storage chambers 173 and 173' permeate through the semipermeable films 176, are transferred to the brain tissue by electrophoresis, and reach the morbid portion. Ultrasonic waves are radiated from probes 180 connected to an ultrasonic generator 179 to the morbid portion, thereby applying a mechanical stimulus to the cells of the morbid portion. Therefore, the endocytosis of the morbid cells is enhanced to incorporate the administered genes for treatment.

In the apparatus of this embodiment, the gene for treatment can be transferred into a cell located deep in a tissue without mechanically damaging the tissue. This apparatus is particularly effective for gene therapy for a tissue requiring minimum invasion, e.g., a brain. In place of the ultrasonic stimulus used above, a radio wave or microwave may be radiated to heat a morbid cell, thereby enhancing the endocytosis of the cell.

As has been described above, in an apparatus for gene therapy according to the present invention, not only a gene is simply supplied to a cell of a patient, but also a means for assisting to transfer the gene into a cell without depending on natural cellular physiology is arranged. Therefore, the gene can be transferred into a cell located at a target portion of the patient in vivo with a higher probability within a short period of time. The apparatus is applicable to all cell species, thus providing remarkable effects.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An apparatus for gene therapy, comprising:

a probe which is insertable into a body cavity;

supply means provided in said probe for supplying a gene or a gene-packaging particle onto a surface of a human living cell located at a target portion in the body cavity; and a plurality of small needles in said probe and capable of protruding from a distal end of said probe for mechanically forming a plurality of pores in a cell membrane of the human living cell in order to transfer the gene or gene-packaging particle into the cell through the plurality of pores.

2. An apparatus for gene therapy comprising:

a tube having at least a first lumen and a second lumen each of which extends in a direction of an axis of the tube;

a needle member having a plurality of fine needles, sized to form pores in a living cell, which is received in said first lumen and which is located at a distal end of said tube;

driving means for moving the needle member to be protruded out of and returned back into the first lumen;

reservoir means for storing a fluid which contains a suitable gene for the gene therapy, the reservoir means being in fluid communication with said second lumen at a proximal end of said tube; and fluid supply means for supplying the fluid stored in the reservoir means through the second lumen to deliver the fluid from the distal end of the tube.

3. The apparatus according to claim 2, wherein said driving means comprises a piezoelectric element.

4. The apparatus according to claim 2, wherein said driving means comprises a piezoelectric element which deforms when an electric voltage is applied to the piezoelectric element.

5. The apparatus according to claim 2, wherein said fluid supply means comprises a pump.

6. The apparatus according to claim 2, wherein said needle member is positioned such that the member can protrude forward from the distal end of the tube and draw back behind the distal end.

7. The apparatus according to claim 2, wherein said fluid supply means supplies a liquid which contains the gene.

8. The apparatus according to claim 2, wherein said fluid supply means supplies a liquid including fine particles containing the gene.

* * * * *

UNITED STATES PATENT AND TRADEMARK OFFICE
CERTIFICATE OF CORRECTION

PATENT NO. : 5,702,384
DATED : December 30, 1997
INVENTOR(S) : UMEYAMA, et al.

It is certified that error appears in the above-identified patent and that said Letters Patent is hereby corrected as shown below:

Title page, Item [56] References Cited, under "FOREIGN PATENT DOCUMENTS"

"31516830-A1" should be --3516830-A1--

Page 2 of the Title page, column 2, "U.S. PATENT DOCUMENTS"

delete "5,240,885  8/1993  Tomes..........435/287"

Signed and Sealed this

Twelfth Day of January, 1999

Attest:

Attesting Officer     Acting Commissioner of Patents and Trademarks